United States Patent [19]
Kawamoto et al.

[11] Patent Number: 5,519,461
[45] Date of Patent: May 21, 1996

[54] OPTOMETER HAVING OPTOTYPE DISC WHICH ROTATES ABOUT ITS AXIS AND ANOTHER AXIS

[75] Inventors: Hiroshi Kawamoto, Seto; Kazuaki Tange, Owariasahi, both of Japan

[73] Assignee: Tomey Corporation, Japan

[21] Appl. No.: 365,929

[22] Filed: Dec. 29, 1994

[30] Foreign Application Priority Data

Jan. 11, 1994 [JP] Japan .................. 6-001214

[51] Int. Cl.⁶ .................................. G03B 17/00
[52] U.S. Cl. .................................. 351/244; 351/243
[58] Field of Search .................. 351/222, 239, 351/243, 244, 245

[56] References Cited

U.S. PATENT DOCUMENTS

| | | | |
|---|---|---|---|
| 3,355,237 | 11/1967 | Simpson | 351/239 |
| 4,410,243 | 10/1983 | Furste | 351/211 |
| 5,129,720 | 7/1992 | Jovicevic | 351/243 |

FOREIGN PATENT DOCUMENTS

| | | | |
|---|---|---|---|
| 1864517 | 12/1962 | Germany. | |
| 1235622 | 3/1967 | Germany. | |
| 3019729 | 2/1981 | Germany. | |
| 53-3598 | 2/1978 | Japan | A61B 3/09 |

*Primary Examiner*—William L. Sikes
*Assistant Examiner*—James A. Dudek
*Attorney, Agent, or Firm*—Parkhurst, Wendel & Burr

[57] ABSTRACT

An optometer including a main body which has an observation window having a center axis, a rotary optotype disk having circumferentially arranged optotypes and disposed within the main body such that the optotype disk is rotatable about a rotary shaft so that one of the optotypes is brought into alignment with the center axis and viewed through the window, a driving disk rotatable about the center axis and rotatably supporting the rotary shaft such that the rotary shaft is parallel to and radially offset from the center axis, a rotary actuator for rotating the driving disk, and a stationary disk fixed within the main body coaxially with the driving disk and engaging the rotary shaft so as to cause rotation of the optotype disk about the rotary shaft when said driving disk is rotated about the center axis by the rotary actuator.

8 Claims, 6 Drawing Sheets

OPTOMETER HAVING OPTOTYPE DISC WHICH ROTATES ABOUT ITS AXIS AND ANOTHER AXIS

BACKGROUND OF THE INVENTION

1. Field of the Invention

The present invention relates generally to an optometer for an eyesight test, or for measuring the range of vision of an eye under examination, such that a series of optotypes or indicia are presented and viewed through a view finder or observation window formed through the body of the optometer, so that an optometrist can check if a person under examination can correctly recognize the optotypes through the eye. In particular, this invention is concerned with such an optometer which is compact and simple in structure and is capable of presenting a significantly increased number of optotypes to be seen through the window.

1. Discussion of Related Art

A conventional optometer or eyesight testing instrument used for examining the visual acuity of a human eye has a rotary optotype disk which has a plurality of optotypes such as Landolt's Rings, which are arranged in the circumferential direction of the disk. The optotype disk is rotatably supported in the body of the optometer having a window through which the optotypes are viewed by an eye, such that the optotypes are selectively brought into alignment with the window by rotation of the rotary optotype disk.

For enhancing the accuracy and reliability of the an eyesight test, it is desirable to use as many optotypes as possible. However, increasing the number of the optotypes arranged in the circumferential direction of the rotary disk undesirably results in an increased size of the optotype disk itself and an accordingly increased size of the optometer apparatus.

Figure 5:
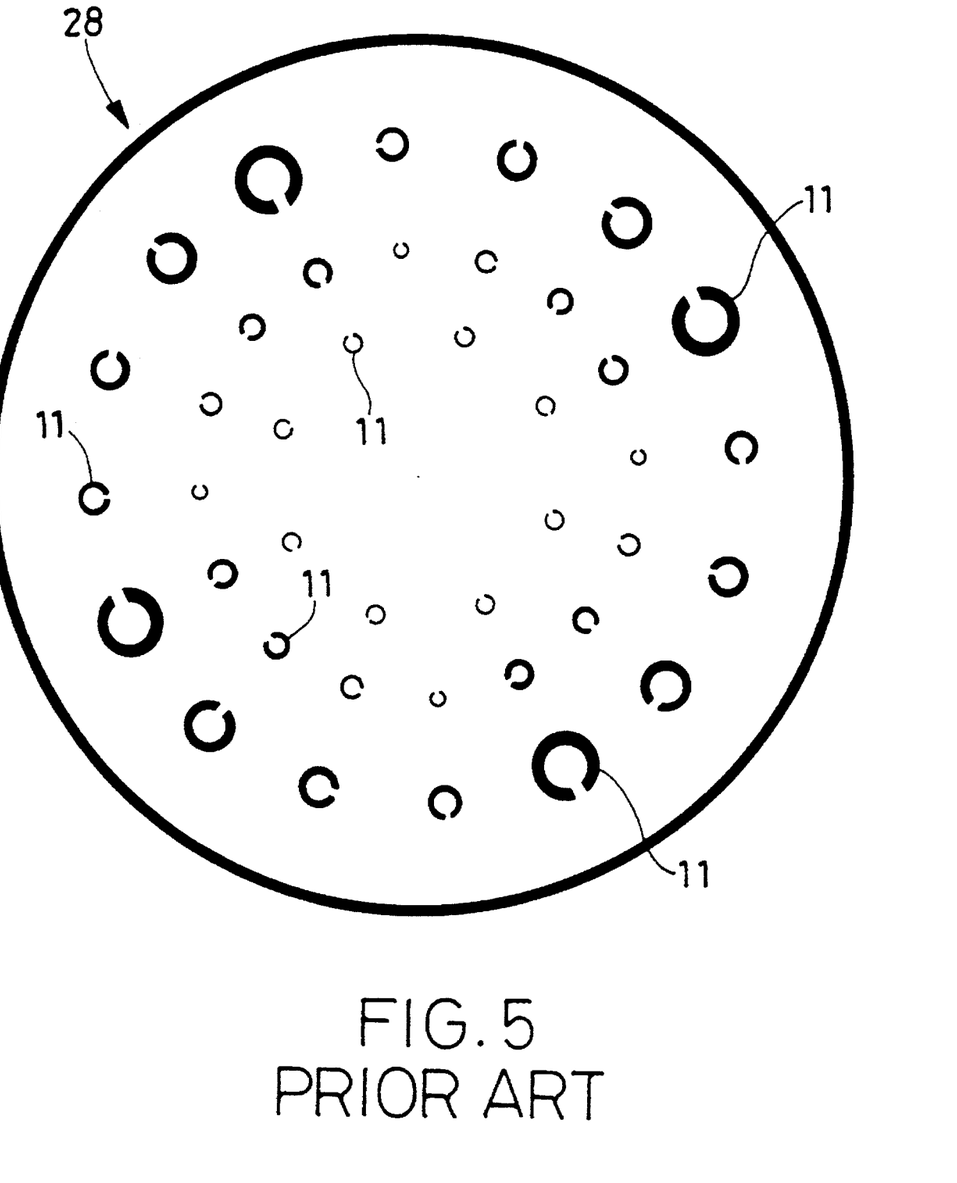
FIG. 5 is a view corresponding to that of FIG. 3, showing an example of a rotary optotype disk which is used in a known optometer.

In the optometer constructed as described above, therefore, various devices and proposals have been made for presenting as many optotypes as possible before a subject person through the observation window, without increasing the size of the apparatus. For example, a relatively large number of optotypes or Landolt's Rings 11 having different sizes and orientations are provided on a rotary optotype disk 28, along a plurality of concentric circles about the center of the disk 28, as shown in FIG. 5. This optotype disk 28 is used with a shutter disk (not shown) which is rotatably disposed between the optotype disk 28 and a wall of the optometer body having the observation window. The shutter disk is dimensioned so as to cover substantially the entire surface area of the optotype disk 28, and has a plurality of openings which correspond to the respective concentric circular arrays of the optotypes 11 on the disk 28. The disk 28 is rotated while a selected one of the openings of the shutter disk is kept in alignment with the window of the optometer, so that the optotypes 11 in the circular array corresponding to the selected opening can be viewed one after another by the eye under examination through the window. With the optometer thus constructed, a relatively large number of optotypes 11 can be provided over the entire area of the front surface of the rotary optotype disk 28, and thus the size of the disk 28 can be advantageously reduced, with a result of reduction in the size of the optometer apparatus as a whole, as compared with a conventional counterpart wherein optotypes are arranged in a single row in the circumferential direction of a rotary optotype disk.

Figure 6:
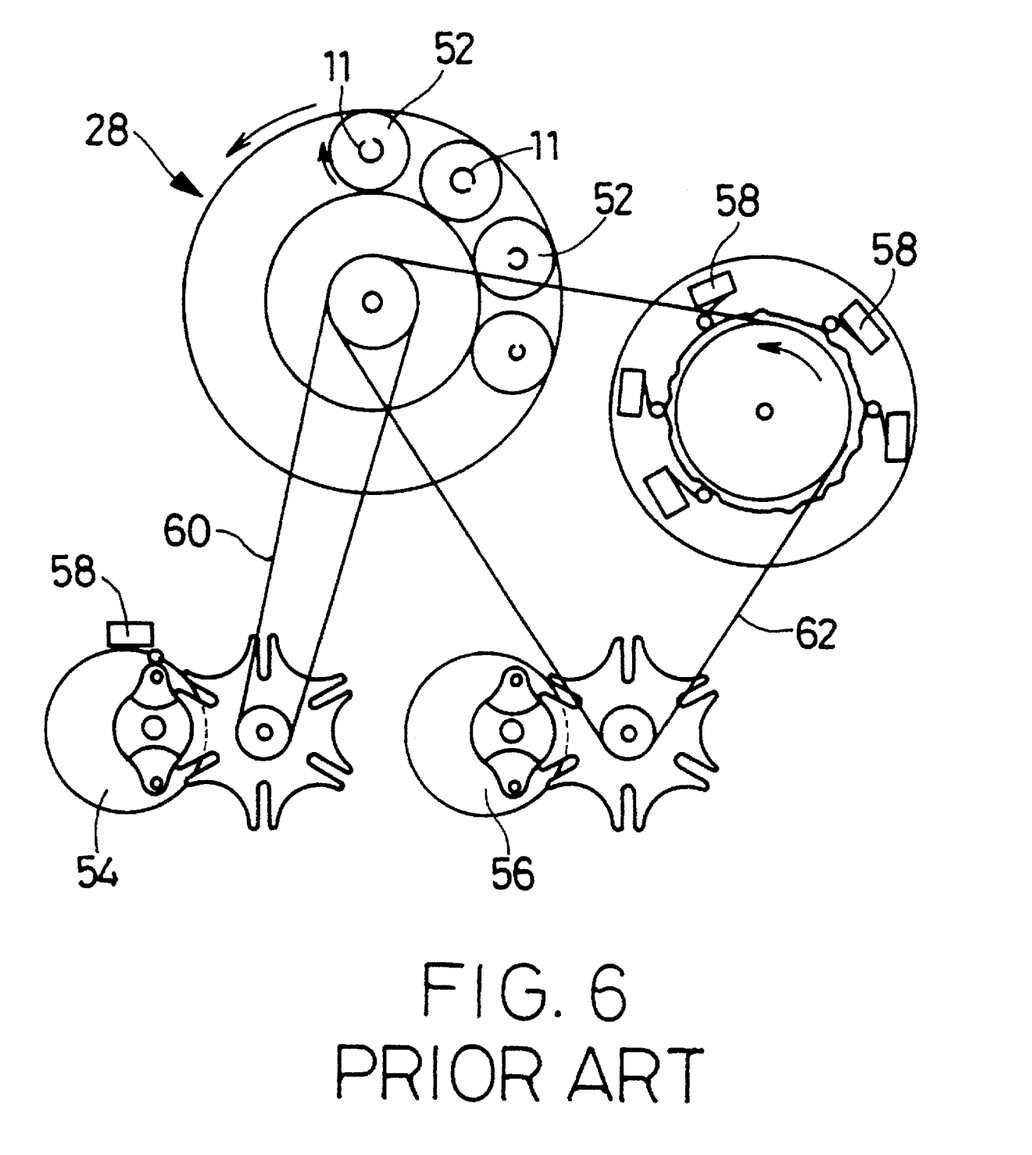
FIG. 6 is a view schematically illustrating an internal structure of another known optometer.

Another example of the optometer is disclosed in JP-B-53-3598, which includes a plurality of optotype disks 52 that are provided with respective optotypes 11 having different sizes, as shown in FIG. 6. These disks 52 are rotatably mounted in the peripheral portion of the rotary disk 28, such that the centers of the disks 52 lie on a circle that is concentric with the rotary disk 28. The rotary disk 28 and the optotype disks 52 are rotated by respective motors 54, 56, through respective chains 60, 62, under the control of limit switches 58, so that a desired one of the optotypes 11 which is oriented as desired is presented through an observation window (not shown). This arrangement eliminates a need to provide the rotary disk 28 with a plurality of optotypes 11 having the same size, and requires a relatively reduced number of optotypes 11, leading to reduction in the sizes of the rotary disk 28 and the optometer itself.

However, the known optometers as described above have various problems. Described more specifically, in the first example as shown in FIG. 5, which uses the rotary optometer disk 28 provided with a large number of optotypes 11 having different sizes and different orientations, no means are provided to reduce the number of optotypes 11 on the disk 28, though the arrangement of the optotypes 11 gives some advantage over the prior apparatus. Therefore, in order to further enhance the accuracy of an eyesight test or vision analysis, for example, a further increased number of optotypes 11 are necessary, thus inevitably increasing the size of the optotype disk 28, and eventually making the optometer apparatus undesirably large-sized. In the second example as shown in FIG. 6, the rotary disk 28 is provided with the optotype disks 52 the number of which is equal to the number of the optotypes 11 required, and the rotary disk 28 and the optotype disks 52 are rotated by the respective motors 54, 56. This inevitably makes the optometer structure undesirably complicated.

SUMMARY OF THE INVENTION

It is therefore an object of the present invention to provide a compact, simple optometer with a reduced number of components, which has a required minimum number of optotypes on a rotary optotype disk, and which is capable of changing the orientation of each optotype.

The above object may be accomplished according to the principle of the present invention which provides an optometer comprising: (a) a main body which has an observation window having a center axis; (b) a rotary optotype disk having a plurality of optotypes arranged in a circumferential direction thereof, the optotype disk being disposed within the main body such that the optotype disk is rotatable about a rotary shaft so that one of the optotypes is brought into alignment with the center axis and viewed through the observation window; (c) a driving disk which is rotatable about the center axis of the window and which rotatably supports the rotary shaft of the rotary optotype disk such that the rotary shaft is parallel to and radially offset from the center axis; (d) a rotary actuator for rotating the driving disk; and (e) a stationary disk fixed within the main body coaxially with the driving disk and engaging the rotary shaft of the optotype disk so as to cause rotation of the optotype disk about the rotary shaft when the driving disk is rotated about the center axis by the rotary actuator.

In the optometer constructed according to the present invention as described above, the rotary optotype disk is rotatably supported by the driving disk which is rotatable about the center axis of the observation window of the main body, such that the rotary optotype disk is rotatable about a rotary shaft which is parallel to and radially offset from the center axis of the window. Further, the rotary optotype disk engages the stationary disk which is fixed within the main body in coaxial relationship with the driving disk, so that the optotype disk is rotated about the rotary shaft when the driving disk is rotated about the center shaft by the rotary actuator. Described in detail, a rotary motion of the driving disk which rotatably supports the rotary shaft causes the rotary shaft and the optotype disk to revolve around the center axis of the observation window. A revolving motion of the rotary shaft around the center axis causes the rotary shaft to be rotated in engagement with the stationary disk, whereby the optotype disk is rotated about the rotary axis. Thus, the optotypes provided on the rotary plate can be selectively brought into alignment with the observation window one after another as the optotype disk revolves about the center axis and rotates about the rotary shaft. Further, the orientation of the same optotype which is aligned with and viewed through the window is changed depending upon the number of rotations of the optotype disk about its own axis, that is, the rotary axis, while the optotype disk is revolved around the center axis.

The above-described arrangement makes it possible to present each of the optotypes in two or more different orientations or directions as viewed through the window of the main body. The number of the different orientations of each optotype can be changed by changing the number of rotations of the optotype for one revolution of the optotype disk, that is, by changing the ratio of the diameter of the stationary disk to that of a portion of the rotary shaft which engages the stationary disk. Consequently, the present optometer does not require the optotype disk to have a plurality of optotypes having the same size and different orientations or postures. Thus, the number of the different optotypes (different in size and/or shape but having the same orientation) can be reduced to a required minimum.

In the optometer of the present invention, the optotypes are directly provided on the optotype disk, and the rotation and revolution of the optotype disk can be carried out by rotation of the driving disk by only one rotary actuator such as a motor. Therefore, the number of components required to rotate and revolve the optotype disk is advantageously reduced as compared with that of a conventional counterpart.

With the numbers of the optotypes and components reduced as described above, the size of the rotary optotype disk and the required space for installation of the components in the main body can be effectively reduced, whereby the present optometer can be small-sized and made compact and inexpensive as compared with the conventional counterpart, yet the present optometer is capable of presenting optotypes in a large number of combinations of size (shape) and orientation (posture).

In one preferred form of the present invention, the rotary shaft of the optotype disk has a first gear portion while the stationary disk has a second gear portion at a periphery thereof. These first and second gear portions engage with each other so that the optotype disk is rotated about the rotary shaft while revolving around the stationary disk when the driving disk is rotated by the rotary actuator. Namely, the first gear portion functions as a rotary planetary gear while the second gear portion functions as a stationary sun gear. This arrangement assures accurate and reliable control of the rotating motion of the optotype disk about its own axis with respect to the revolving motion of the optotype disk around the center axis, whereby the desired ones of the optotypes can be accurately aligned with the observation window as the driving disk is rotated by the rotary actuator. In this respect, it is noted that the number of teeth of the second gear portion (stationary sun gear) is a multiple of the number teeth of the first gear portion (rotary planetary gear).

In another preferred form of the invention, the rotary actuator has a drive shaft which is geared with a peripheral portion of the driving disk, through a suitable gearing mechanism. For instance, the drive shaft has a pinion which meshes with the driving disk in the form of a spur gear. The use of this gearing mechanism assures accurate control of the rotating motions of the driving disk and the optotype disk, and permits considerable reduction of the spacing between the rotary actuator and the driving disk, leading to further reduction of the overall size of the optometer.

In a further preferred form of the invention, the observation window is located at a generally central portion of the main body. In this case, the field of view of an eye under examination can be easily confined to a view within the observation window, with reduced adverse influences of the environment of the optometer, such as an influence of a difference in brightness between the walls surrounding the optometer and the view within the window. This leads to enhanced accuracy of an eyesight test by the optometer. Further, the axis about which the optotype disk revolves is aligned with the center axis of the observation window located at or near the central portion of the main body. This arrangement is effective to reduce the overall size of the optometer. In the known optometer shown in FIG. 6, the axis about which the optotype disks 52 is revolved is offset from the center axis of the observation window, and the overall size of the optometer tends to be large.

In a still further preferred form of this invention, the optometer further comprises a stationary sleeve which is disposed within the main body coaxially with the center axis of the window, on one of opposite sides of the optotype disk remote from the observation window. In this case, the driving disk is rotatably mounted on the stationary sleeve, while the stationary disk is fixedly attached to the stationary sleeve coaxially with the driving disk. A light source is preferably disposed within the stationary sleeve, for illuminating a portion of the optotype disk which is aligned with the observation window. This arrangement does not require an exclusive space for installation of the light source, and does not increase the size of the optometer.

A detector may be disposed adjacent to the driving disk for detecting a reference angular position of the optotype disk in which each of the plurality of optotypes has a predetermined orientation.

While the optometer of the present invention which has been described above uses only one optotype disk, the present invention is equally applicable to an optometer having two or more optotype disks which are coaxial with each other and are rotatable independently of each other. In this case, each optotype disk is provided with a cutout formed in a circumferential portion thereof, so that the cutout of each disk permits the optotypes on the other optotype disk or disks to be viewed through the observation window.

BRIEF DESCRIPTION OF THE DRAWINGS

The above and optional objects, features and advantages of the present invention will be better understood by reading the following detailed description of presently preferred embodiments of the invention, when considered in connection with the accompanying drawings, in which.

DETAILED DESCRIPTION OF PREFERRED EMBODIMENTS

Figure 1:
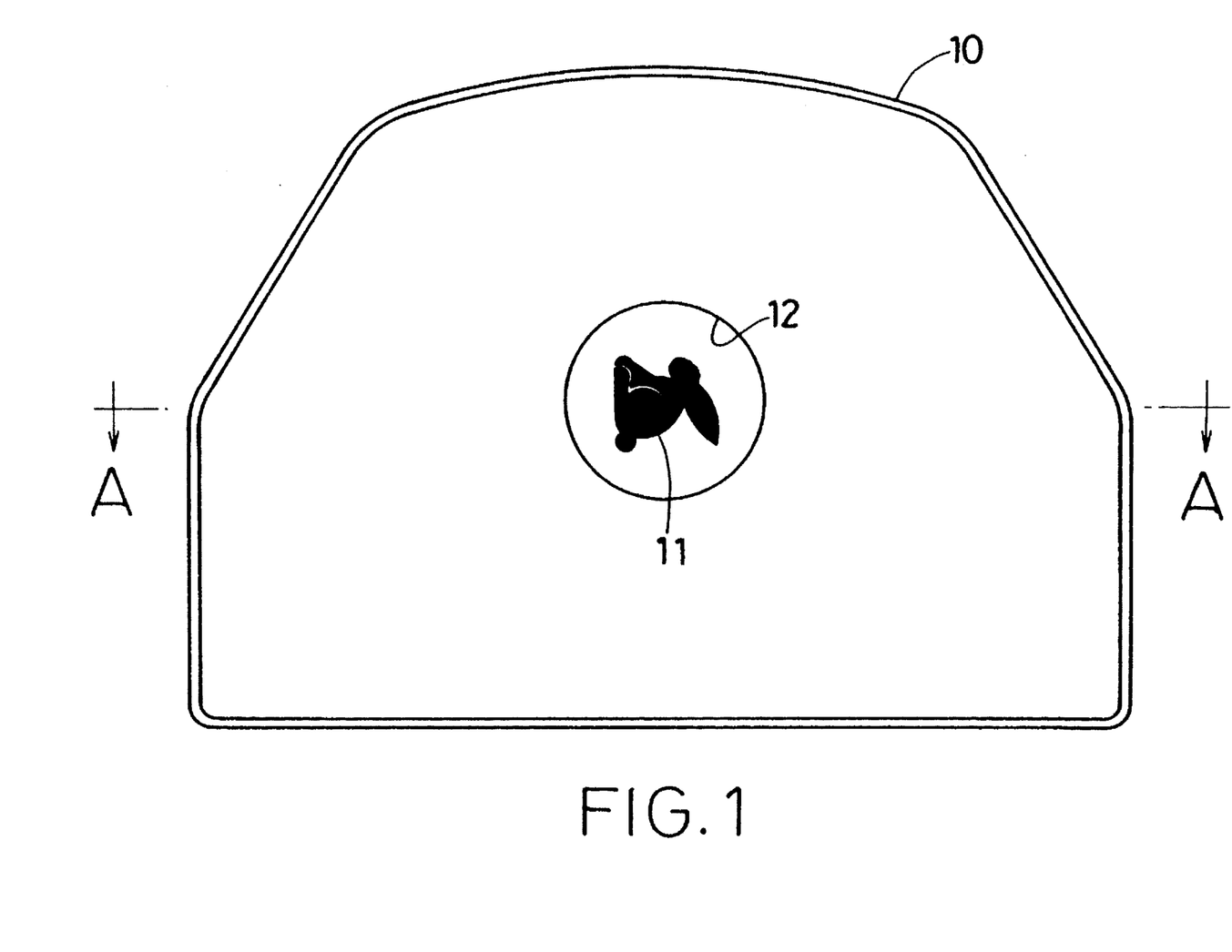
FIG. 1 is a front view showing one embodiment of an optometer of the present invention.
Figure 2:
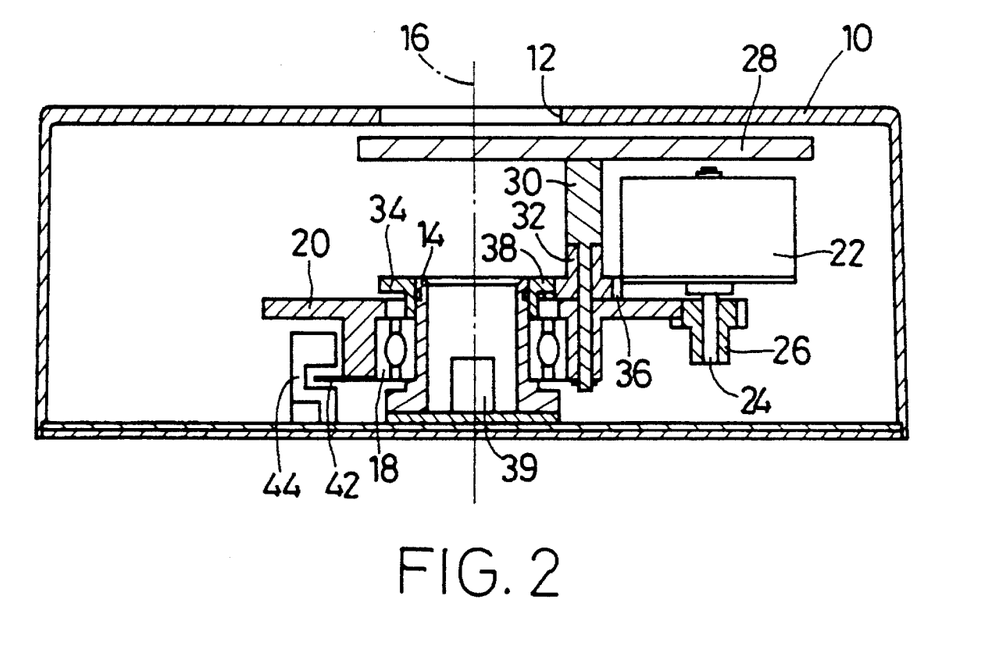
FIG. 2 is a cross sectional view taken along line A—A of FIG. 1.

Referring first to FIGS. 1 and 2 schematically showing a preferred embodiment of an optometer of the present invention, a main body 10 of the optometer has a generally rectangular shape with a trapezoidal upper half, and has a circular observation window 12 formed through a substantially or generally central portion thereof. As described below in detail, a selected one of optotypes 11 is viewed by an eye of a subject person through the window 12 of the main body 10.

The main body 10 of the optometer incorporates a generally cylindrical, stationary sleeve 14 which is fixedly disposed coaxially with a center axis 16 of the window 12 of the body 10. Lamp 39 serving as a light source is disposed at the bottom of an inner bore of the stationary sleeve 14. Further, a gear 20 which serves as a driving disk is rotatably mounted on an axially middle portion of the stationary sleeve 14, through a bearing 18.

On one side of the stationary sleeve 14, there is fixedly disposed a rotary actuator in the form of a motor 22 which has a drive shaft 24 and is adapted to rotate the gear 20. To the drive shaft 24, there is fixed a gear 26 which meshes with the gear 20. In this arrangement, the gear 20 is rotated by the motor 22 about the center axis 16 of the window 12 of the main body 10.

Figure 3:
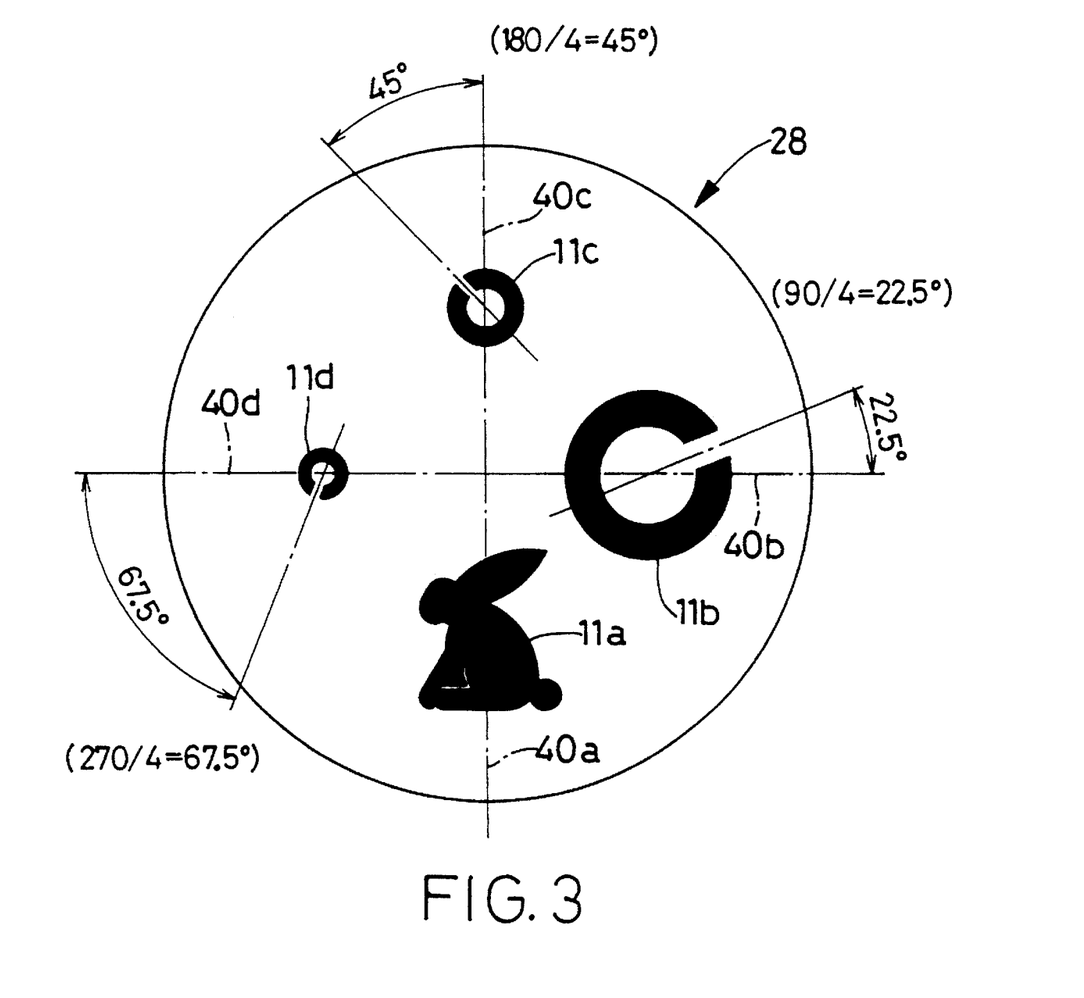
FIG. 3 is a front view showing one example of a rotary optotype disk provided with optotypes, which disk is used in the optometer of FIG. 1.

The main body 10 also incorporates a rotary optotype disk 28 a part of which is located between the window 12 and the stationary sleeve 14 fixed within the main body 10. This optotype disk 28 is a relatively large-diameter disk-shaped member, and has a plurality of optotypes 11 provided on one of its opposite major surfaces which faces the window 12, as shown in FIG. 3. Rotary shaft 30 is fixed to the optotype disk 28, at the center of the major surface of the optotype disk 28 on the side of the stationary sleeve 14, such that the shaft 30 extends toward the gear 20 in parallel with the center axis 16 of the window 12 of the main body 10. The rotary shaft 30 is radially offset by a predetermined distance from the center axis 16. The rotary shaft 30 has a distal end portion which is rotatably attached to a thick-walled, radially inner portion of the gear 20.

Small-sized rotary disk 32 is fixed to an axially middle portion of the rotary shaft 30, while large-sized stationary disk 34 is fixed to one axial end portion of the stationary sleeve 14 on the side of the optotype disk 28. These rotary and stationary disks 32, 34 are toothed at their peripheries, that is, have gear portions 36, 38, respectively, which engage each other. In this arrangement, when the gear 20 is rotated by the motor 22 about the center axis 16 of the window 12, the optotype disk 28 is revolved about the center axis 16, with the rotary disk 32 engaging the stationary disk 34, whereby the optotype disk 28 is rotated about its own axis, namely, about the axis of the rotary shaft 30. Thus, the stationary disk 34 acts as a stationary sun gear while the rotary disk 32 acts as a rotary planetary gear.

Further, shielding plate 42 and a photoelectric sensor 44 are provided within the optometer, in the vicinity of the wall of the main body 10 to which the stationary sleeve 14 is fixed. The shielding plate 42 is attached to the thick-walled radially inner portion of the gear 20, at a predetermined angular or circumferential position of the gear 20. The photoelectric sensor 44 has a light-emitting element and a light-sensitive element, and is disposed so as to sandwich the shielding plate 42. This photoelectric sensor 44 is adapted to detect the predetermined angular position of the gear 20, which corresponds to a reference or zero position of the optotype disk 28 which will be described later. In this embodiment, the motor 22 for rotating the gear 20 consists of a stepping motor which operates in steps in response to input pulses received from a suitable controller (not shown) so as to drive or rotate the gear 20 via the drive shaft 24 by an angle corresponding to the number of the received input pulses.

When the optometer constructed as described above is in operation for eyesight testing of an eye, the reference position of the optotype disk 28 is initially detected by the photoelectric sensor 44, and then the motor 22 receives a predetermined number of pulses from the controller, so that the optotype disk 28 is rotated about its own axis (axis of the rotary shaft 30) by an amount corresponding to the number of the input pulses, while revolving around the center axis 16, so that an appropriate one of the optotypes 11 is brought into alignment with the window 12 of the main body 10. The optotype 11 thus positioned to be seen through the window 12 is illuminated from behind the optotype disk 28 by the lamp 29 located in the inner bore of the stationary sleeve 14, and can therefore be clearly viewed by the eye under examination.

In the instant embodiment, in particular, the optotypes 11 consist of one reference optotype 11a in the form of a rabbit, and three Landolt's Rings 11b, 11c and 11d having different sizes, as shown in FIG. 3. These optotypes 11 have predetermined orientations when the disk 28 is placed in its reference position, and are located at respective four predetermined positions which lie on the same circle on the surface of the optotype disk 28 on the side of the window 12.

Referring to FIG. 3, center lines 40a, 40b, 40c and 40d connect the center of the optotype disk 28 with the centers of the optotypes 11a, 11b, 11c and 11d, respectively. The optotypes 11 are located on the same circle on the optotype disk 28 such that these center lines 40a, 40b, 40c, 40d intersect at right angles with each other, at the center of the disk 28. The reference optotype 11a in the form of a rabbit is oriented such that the center line 40a passes a head and legs of the rabbit having a sitting posture, with the head being located below the center of the optotype disk 28 and the legs directing toward the periphery of the disk 28. The three Landolt's rings 11b, 11c, 11d have respective openings or cutouts which are formed at predetermined circumferential positions thereof. Those cutouts are spaced apart from the center lines 40b, 40c, 40d in the counterclockwise direction of the optotype disk 28. Described more specifically, one-dot chain lines (as shown in FIG. 3) passing the cutouts and centers of the Landolt's Rings 11b, 11c, 11d form 22.5°, 45° and 67.5°, respectively, with respect to the corresponding center lines 40b, 40c, 40d. The angular value indicating the position of the cutout of each ring 11b, 11c, 11d is calculated by dividing an angle (90°, 180° or 270°) formed between the center lines 40a passing the rabbit 11a and each of the center lines 40b, 40c, 40d, by the ratio (4 in this embodiment) of the diameter of the large-sized stationary disk 34 to that of the small-sized rotary disk 32. The optotype disk 28 is placed in its reference position when the rabbit 11a as the reference optotype appearing before the window 12 of the main body 10 has the posture or orientation as described above, that is, as shown in FIG. 3.

As described above, the optotype disk 28 revolving around the center axis 16 is rotated about its own axis (axis of the rotary shaft 30) due to the meshing engagement of the large-sized stationary disk 34 fixed to the stationary sleeve 14, with the small-sized rotary disk 32 fixed to the rotary shaft 30. The ratio of the frequency of the rotation of the disk 28 about its axis to that of the revolution about the axis 16 is represented by the ratio of the diameter of the large-diameter stationary disk 34 to that of the small-sized rotary disk 32. That is, where "M" indicates the diameter of the small-sized rotary disk 32 and "L" indicates the diameter of the large-sized stationary disk 34, the number of rotation of the optotype disk 28 about its own axis during one revolution of the disk 28 about the center axis 16 is equal to L/M. In other words, each of the optotypes 11a, 11b, 11c, 11d passes the window 12 the L/M times while the optotype disk 28 is revolved one full turn (360°) around the center axis 16.

With the four optotypes 11a, 11b, 11c, 11d provided on the optotype disk 28, therefore, the optotype disk 28 is rotated four turns about the rotary shaft 30 while the disk 28 is revolved one turn around the center axis 16, starting from the reference position as shown in FIG. 3. As the optotype disk 28 is thus rotated, the orientation of the rabbit 11a as the reference optotype appearing before the window 12 of the main body 10 is changed such that the legs of the rabbit 11a are directed downward, leftward, upward and rightward, depending upon the number of rotations of the disk 28 about its own axis, i.e., zero (fourth), first, second and third rotations. Similarly, each of the Landolt's Rings 11b, 11c, 11d appears before the window 12 of the main body 10 in different orientations depending upon the number of rotations of the disk 28 about its own axis, such that the ring opens in one of the four (up, down, left and right) directions which corresponds to the current orientation of the rabbit 11a.

In the instant optometer as described above, each of the four optotypes 11a, 11b, 11c, 11d formed directly on the optotype disk 28 can be presented and viewed through the window 12 of the main body 12 in a selected or desired one of the four orientations or postures, by merely controlling the motor 22 for rotating the gear 20 (large-sized stationary disk 34) by an appropriate angle, which causes the optotype disk 28 to rotate about the rotary shaft 30 while revolving about the center axis 16. Thus, the present optometer which has a compact, simple and inexpensive structure can be considered to present as many as 16 kinds of optotype indicia while only four optotypes 11a–11d are actually provided on the optotype disk 28.

In the instant embodiment, the ratio of the number of rotations of the disk 28 about its own axis to that of revolution about the center axis 16 determines the number of possible orientations in which each optotype 11 is presented and viewed through the observation window 12. This number of possible orientations of each optotype 11 is determined by the ratio of the diameter of the large-diameter stationary disk 34 to that of the small-sized rotary disk 32. Accordingly, the total number of optotype indicia (number of types multiplied by number of orientations of each type) which are available on the optometer can be increased by increasing the ratio of the diameters of the large-sized stationary disk 34 and the small-sized rotary disk 32.

The present arrangement wherein the rotation of the gear 20 causes both the rotation of the disk 28 about its own axis and the revolution of the same about the axis of the window 12 permits easy presentation of a desired one of the four optotypes 11 in a desired one of the four possible orientations, as viewed through the observation window 12 with which the desired optotype 11 can be readily aligned by suitably controlling the angle of rotation of the gear 20.

Further, in the instant embodiment, the gear 20 engages the gear 26 attached to the drive shaft 24 of the motor 22, while the gear portion 36 of the small-sized rotary disk 32 fixed to the rotary shaft 30 of the optotype disk 28 engages the gear portion 38 of the large-sized stationary disk 34 disposed coaxially with the center axis 16 about which the optotype disk 28 is revolved. In this arrangement, as the gear 20 is rotated by the motor 22 about the center axis 16, the optotype disk 28 is rotated about the rotary shaft 30 while being revolved about the center axis 16. Thus, the above-described gearing arrangement not only assures high operating reliability of rotation and revolution of the optotype disk 28 about its own axis and the center axis 16, respectively, but also permits the motor 22 to be located relatively close to the gear 20, thereby reducing the overall size of the optometer.

Moreover, a desired one of the optotypes 11 can be viewed through the window 12 of the main body 10 of the present optometer owing to the revolving or orbital motion of the optotype disk 28 around the center axis 16 of the window 12. Accordingly, the window 12 can be formed through a generally middle portion of the main body 10 of the optometer, without increasing the size of the main body 10. This location of the window 12 is effective to confine a field of view of an eye under examination to a view within the window 12, while reducing undesirable influences of the environment of the optometer on the subject eye, whereby the accuracy of an eyesight test by the present optometer is improved.

In the instant embodiment, the lamp 39 for illuminating the optotype 11 aligned with the window 12 is installed in the inner bore of the stationary sleeve 14 fixed within the main body 10, so as to allow the eye under examination to clearly observe the relevant optotype 11. Therefore, the location of the lamp 39 does not require an exclusive space for installation of the lamp 39, thus making the obtained optometer compact or small-sized.

While the present invention has been described in its preferred embodiment, for illustrative purpose only, it is to be understood that the invention is not limited to the details of the illustrated embodiment, but may be otherwise embodied.

In the illustrated embodiment, the reference position of the optotype disk 28 is detected by the photoelectric sensor 44, while the revolution and rotation of the optotype disk 28 are regulated by the motor 22 in the form of a stepping motor. However, any other known devices may be suitably employed for regulating the rotation of the optotype disk 28. For example, a rotary encoder may be used for detecting the reference position of the optotype disk. However, such means for detecting the reference position of the optotype disk is not essential to the present invention.

In the illustrated embodiment, the plurality of optotypes 11 provided on the optotype disk 28 consist of a rabbit indicia 11a serving as the reference optotype, and three Landolt's Rings 11b, 11c, 11d. However, the number and shapes of the optotypes may be suitably changed as needed, depending upon the size and shape of the optotype disk, for example. Further, the shape of the reference optotype may be the same as that of the other optotypes.

In the illustrated embodiment, the ratio of the diameter of the large-sized stationary disk 34 to that of the diameter of the small-sized rotary disk 32, that is, the number of rotations of the optotype disk 28 about its own axis for one full revolution of the same is equal to "4", and each of the optotypes 11a, 11b, 11c, 11d is presented in four orientations (upward, downward, leftward and rightward postures), through the window 12 of the main body 10. However, the ratio of the diameter of the large-sized disk to that of the small-sized disk is not limited to "4", but may be changed as needed, depending upon the required number of orientations or postures of the optotype as viewed through the window 12.

Figure 4:
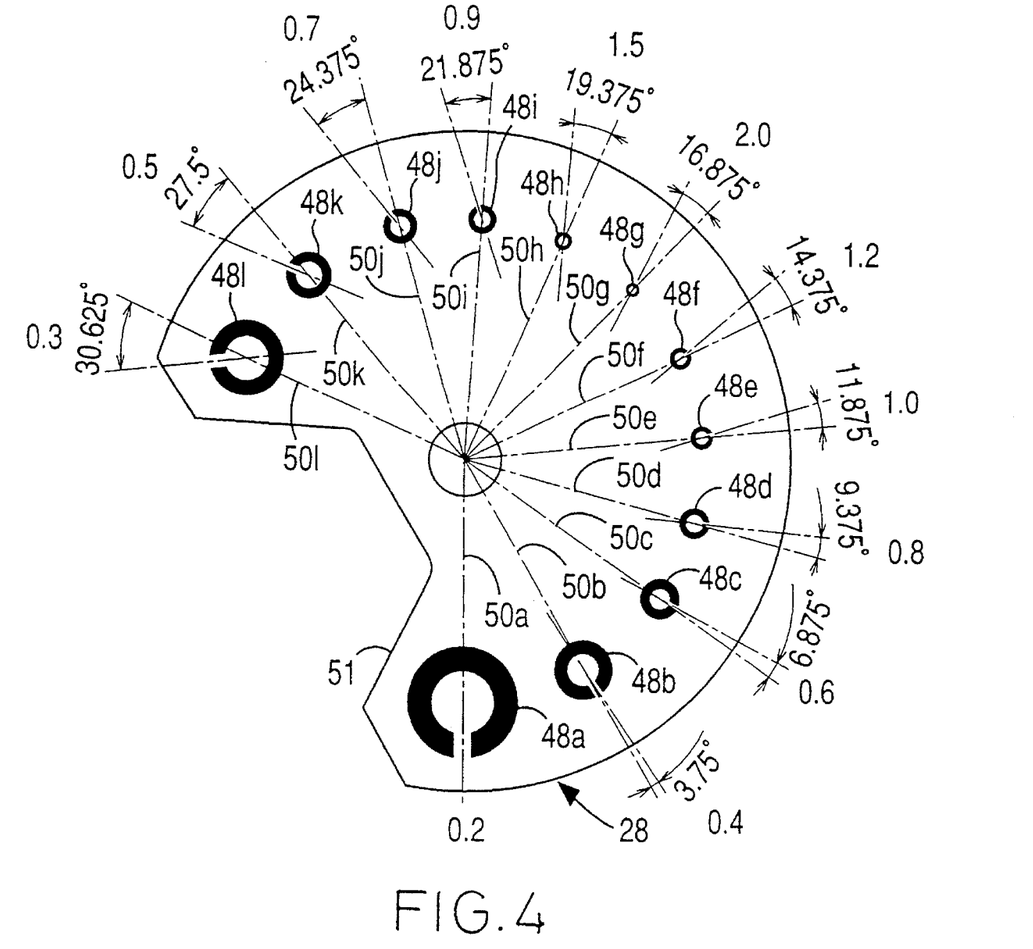
FIG. 4 is a view corresponding to that of FIG. 3, showing another example of the rotary optotype disk usable in the testing apparatus of FIG. 1.

In the illustrated embodiment, the optotypes 11 are provided along the circumference of the optotype disk 28, such that the optotypes 11 are spaced equiangularly from each other in the circumferential direction, and are inclined at predetermined angles (22.5°, 45°, 67.5°) with respect to the center lines which pass the centers of the respective optotypes and the center of the disk 28. However, the arrangement of the optotypes on the optotype disk is by no means limited to that of the illustrated embodiment. For example, the optotype disk 28 as shown in FIG. 4 is provided with twelve optotypes 48a–48l, which are angularly spaced by different angles from each other in the circumferential direction of the disk 28, and are inclined at predetermined angles (corresponding to the above different angles) with respect to center lines 50a–50l which pass the centers of the respective optotypes 48a–48l and the center of the disk 28.

In the illustrated embodiment, the optotype disk 28 consists of a single disk of a relatively large diameter having the optotypes 11 on one of its opposite major surfaces, and is fixed to the rotary shaft 30 that is rotatably supported by and attached to the gear 20 as a driving member for rotating and revolving the disk 18. However, a plurality of such optotype disks may be attached to a rotary shaft. For example, a plurality of optotype disks 28 as shown in FIG. 4 may be mounted on a common shaft such that the disks 28 are spaced apart from each other in the axial direction of the common shaft and such that the disks 28 are rotatable about the common shaft independently of each other. Each of these disks 28 has a plurality of optotypes 48, and a cutout 51 at a circumferential portion thereof. In this arrangement, a desired one of the optotypes 48 provided on the first optotype disk 28 which is located closest to the window 12 of the main body 10 is presented through the window 12 by rotating the first optotype disk 28. On the other hand, a desired one of the optotypes 48 provided on the second optotype disk 28 which is located behind the first disk 28 remote from the window 12 is presented through the cutout 51 of the first disk 28 and the window 12, by rotating the second optotype disk 28 while holding the first optotype disk 28 in a predetermined position where the cutout 51 is in alignment with the window 12. In the same manner, each of the optotypes 48 provided on the third and following optotype disks 28 located behind the second disk 28 can be presented and viewed through the window 12 and the cutouts 51 of the disks 28 in front of the disk 28 in question. This makes it possible to increase the number of optotypes which can be viewed through the window of the optometer, without increasing the size of the optotype disks 28 and the size of the optometer itself.

It is to be understood that the present invention may be embodied with various other changes, modifications and improvements, which may occur to those skilled in the art, without departing from the scope of the invention as defined in the following claims.

What is claimed is:

1. An optometer comprising:
   a main body which has an observation window having a center axis;
   a rotary optotype disk having a plurality of optotypes arranged in a circumferential direction thereof, said optotype disk being disposed within said main body such that said optotype disk is rotatable about a rotary shaft so that one of said optotypes is brought into alignment with said center axis and viewed through said observation window;
   a driving disk which is rotatable about said center axis of said window and which rotatably supports said rotary shaft of said rotary optotype disk such that said rotary shaft is parallel to and radially offset from said center axis;
   a rotary actuator for rotating said driving disk; and
   a stationary disk fixed within said main body coaxially with said driving disk and engaging said rotary shaft of said optotype disk so as to cause rotation of said optotype disk about said rotary shaft when said driving disk is rotated about said center axis by said rotary actuator.

2. An optometer according to claim 1, wherein said rotary shaft of said optotype disk has a first gear portion while said stationary disk has a second gear portion at a periphery thereof, said first and second gear portions engaging with each other so that said optotype disk is rotated about said rotary shaft while revolving around said stationary disk when said driving disk is rotated by said rotary actuator.

3. An optometer according to claim 1, wherein said rotary actuator has a drive shaft which is geared with a peripheral portion of said driving disk.

4. An optometer according to claim 1, wherein said observation window is located at a generally central portion of said main body.

5. An optometer according to claim 1, further comprising a stationary sleeve which is disposed within said main body coaxially with said center axis of said window, said driving disk being rotatably mounted on said stationary sleeve, and said stationary disk being fixedly attached to the stationary sleeve coaxially with said driving disk.

6. An optometer according to claim 5, wherein said stationary sleeve is located on one of opposite sides of said optotype disk remote from said observation window, said optometer further comprising a light source disposed within said stationary sleeve, for illuminating a portion of said optotype disk which is aligned with said observation window.

7. An optometer according to claim 1, further comprising a detector disposed adjacent to said driving disk for detecting a reference angular position of said optotype disk in which each of said plurality of optotypes have a predetermined orientation.

8. An optometer according to claim 2, wherein said second gear portion of said stationary disk has a diameter which is a multiple of a diameter of said first gear portion of said rotary shaft of said optotype disk.

* * * * *